(12) United States Patent
Breuilh et al.

(10) Patent No.: US 11,883,021 B2
(45) Date of Patent: Jan. 30, 2024

(54) SURGICAL SYSTEM PROVIDING A REVERSIBLE CONNECTION BETWEEN TWO IMPLANTS OR BETWEEN AN IMPLANT AND A TOOL OF THE SURGICAL SYSTEM

(71) Applicants: IMPRINT MEDICAL, Brignais (FR); EUCLIDE CARE, Aixe sur Vienne (FR)

(72) Inventors: Christophe David Breuilh, Panazol (FR); Didier Julien Guillon-Cottard, Oullins (FR)

(73) Assignees: IMPRINT MEDICAL, Brugnais (FR); EUCLIDE CARE, Aixe sur Vienne (FR)

( * ) Notice: Subject to any disclaimer, the term of this patent is extended or adjusted under 35 U.S.C. 154(b) by 0 days.

(21) Appl. No.: 17/993,859

(22) Filed: Nov. 23, 2022

(65) Prior Publication Data
US 2023/0157686 A1    May 25, 2023

(30) Foreign Application Priority Data

Nov. 24, 2021   (FR) ..................................... 2112449

(51) Int. Cl.
*A61B 17/068*   (2006.01)
*A61B 17/00*    (2006.01)
(52) U.S. Cl.
CPC .. *A61B 17/068* (2013.01); *A61B 2017/00398* (2013.01)
(58) Field of Classification Search
None
See application file for complete search history.

(56) References Cited

U.S. PATENT DOCUMENTS 6,183,472 B1 * 2/2001 Lutz ................... A61B 17/7086
606/279
7,278,995 B2 * 10/2007 Nichols .............. A61B 17/7032
606/272

(Continued)

FOREIGN PATENT DOCUMENTS

WO   WO-2008/039981 A2   4/2008
WO   WO-2020/206316 A1   10/2020

OTHER PUBLICATIONS

Search Report issued in FR 2112449, dated Jul. 13, 2022.

*Primary Examiner* — Nathaniel C Chukwurah
(74) *Attorney, Agent, or Firm* — MARSHALL, GERSTEIN & BORUN LLP (57) ABSTRACT

A surgical system includes first and second elements. The first element has a first bearing face and a first helical surface extending from the first bearing face. The second element comprises a second bearing face, complementary to the first bearing face, a second helical surface extending from the second bearing face and congruent with the first helical surface so that the helical surfaces form a helical connection centered on an axis, and a mechanism for controlling reversible connection between the elements, the mechanism being suitable for successively actuating according to a first movement, which includes an axial translation without involving any rotation and by which the mechanism meshes the helical surfaces until the bearing faces are axially juxtaposed, a second movement, which is a rotation about the axis and by which the mechanism locks the helical connection while the bearing faces are pressed axially against each other.

14 Claims, 9 Drawing Sheets

(56) References Cited

U.S. PATENT DOCUMENTS

| | | | |
|---|---|---|---|
| 8,540,718 B2 * | 9/2013 | Dauster | A61B 17/1757 606/86 A |
| 9,265,533 B2 * | 2/2016 | Nelson | A61B 17/7091 |
| 2007/0233249 A1 | 10/2007 | Shadduck | |
| 2009/0319043 A1 | 12/2009 | McDevitt et al. | |

* cited by examiner

SURGICAL SYSTEM PROVIDING A REVERSIBLE CONNECTION BETWEEN TWO IMPLANTS OR BETWEEN AN IMPLANT AND A TOOL OF THE SURGICAL SYSTEM

FIELD

The present invention relates to a surgical system comprising two elements, which are either two surgical implants or a surgical implant and a surgical instrument, and which incorporate respective arrangements for the reversible connection thereof.

BACKGROUND

During various operations carried out in connection with a surgical procedure, it is necessary to connect to each other, in a reversible manner, either surgical implants or a surgical implant and a surgical instrument. When placing a surgical implant e.g. in the body of a patient, the surgeon uses an ancillary device for successively connecting the implant to the ancillary device, positioning, by force where appropriate, the implant in the body of the patient by manipulating the ancillary device, and then detaching the implant in place from the ancillary device. In practice, various embodiments are known for the respective arrangements of the two surgical elements, providing the reversible connection between the latter.

One of the embodiments, which is currently widespread, consists of a threaded connection between the surgical elements: one of the two elements thus incorporates a mechanism having a threaded projecting rod, while the other element is provided with a threaded hole into which the threaded rod is to be screwed so as to provide the connection between the two elements. However, such a threaded connection is not satisfactory in several respects. First, the surgeon is forced, while screwing the threaded rod into the tapped hole, to hold the two elements in place, while rotating the rod for a plurality of turns. The corresponding movements of the surgeon are thus relatively complicated, generally by mobilizing both hands, and take a considerable intraoperative time. The threaded connection then carries the risk of not being sufficiently secured: during the surgical intervention, the two elements have a risk of accidental detachment from each other and/or the connection therebetween has a risk of breaking if large forces are applied, e.g. during bending or impaction. Finally, such a threaded connection comes with constraints when made by additive manufacturing: when the surgical elements are produced by additive manufacturing, the latter generally does not make it possible, for lack of precision, to directly obtain the thread and the tapping of the threaded connection, to the extent that it is necessary to alter the manufactured elements, by implementing conventional rework or alteration operations, e.g. machining operations using a tool. Such additional alteration or rework operations can be complex to implement, carry the risk of contaminating the surgical elements, e.g. by cutting oils, and entail a significant additional cost.

SUMMARY

The purpose of the present invention is to propose a new surgical system in which the reversible connection of two elements is both simpler to operate, more secure and with less manufacturing constraints, in particular when the elements are made by additive manufacturing.

To this end, the invention relates to a surgical system, comprising first and second elements that are either two surgical implants, or a surgical implant and a surgical instrument. The first element has a first bearing face and a first helical surface extending from the first bearing face. The second element includes a second bearing face, which is complementary to the first bearing face, and a second helical surface, which extends from the second bearing face and which is congruent with the first helical surface so that the first and second helical surfaces form a first helical connection between the first and second elements, centered on an axis. The second element also includes a mechanism for controlling reversible connection between the first and second elements, the mechanism being suitable for being actuated successively: along a first movement, which includes a translation along the axis without involving rotation about the axis and by which the mechanism causes the first and second helical surfaces to mesh with each other until the first and second bearing faces are axially juxtaposed against each other, and along a second movement, which includes a rotation about the axis and by which the mechanism locks the first helical connection while the first and second bearing faces are pressed axially against each other.

One of the ideas underlying the invention is to seek to provide the connection of the two elements of the surgical system not by a threaded connection, but by a helical connection the helical surfaces of which forming the helical connection do not have to be a conventional thread and a conventional tapping. In the system according to the invention, the helical connection is formed by two helical surfaces that are delimited by one and the other of the two elements, respectively, extending from respective bearing faces of the two elements. Moreover, the system according to the invention, comprises a mechanism which is integrated into one or the other of the two elements and which is designed to be actuated according to two simple and rapid movements made by the surgeon, typically with one hand, namely a first movement which includes a translation along the axis of the helical connection, without involving any rotation about the axis, and a second movement which includes a rotation about the axis, potentially being combined with a translational component along the axis. The mechanism and the two helical surfaces of the helical connection are configured such that when the mechanism is actuated according to the first movement, the mechanism acts on the helical connection by meshing the two helical surfaces with each other until the aforementioned bearing faces of the two elements come into axial abutment and then when the mechanism is actuated according to the second movement, the mechanism acts on the helical connection for locking same while the two bearing faces are pressed firmly against each other along the axis, which secures the connection between the two elements. Insofar as the two helical surfaces do not have to be produced in the form of a conventional thread and a conventional tapping, which would form a threaded connection, the two helical surfaces and, more generally, the two elements of the system can be made by additive manufacturing without requiring any alteration or rework, in particular by machining. In practice, since the two surgical elements of the system according to the invention are either two implants, or an implant and an instrument, the helical connection and the mechanism acting on the latter impart a great suitability of use to the elements, in particular in relation to the patient operated on and/or the surgical approach and/or the surgical technique.

According to advantageous additional features of the surgical system according to the invention, taken individually or according to all technically possible combinations:

The first helical connection between the first and second elements has a helix angle comprised between 6° and 45°.

The first helical surface extends recessed inside the first bearing face, and the second helical surface is arranged protruding from the second bearing face.

The second element includes:
- a shaft, which is centered on the axis and which externally delimits the second helical surface, and
- a support which delimits the second bearing face, on which the shaft is mounted both in a fixed manner along the axis and so as to freely rotate about the axis, and on which the mechanism is mounted movable so as to be actuatable according to the first and second movements and to rotate the shaft about the axis with respect to the support when the mechanism is actuated in translation along the axis.

The shaft externally delimits a third helical surface, which is distinct from the second helical surface, and the mechanism delimits a fourth helical surface which is congruent with the third helical surface so that the third and fourth helical surfaces form a helical connection between the shaft and the mechanism.

The mechanism includes an actuating ring, which is guided in motion with respect to the support according to the first and second movements, and the mechanism further includes a drive slide that is:
- linked to the support, in rotation about the axis, while being free in translation along the axis with respect to the support,
- linked to the actuating ring, in translation along the axis, while being free to rotate about the axis with respect to the actuating ring, and
- suitable for rotating the shaft about the axis with respect to the support when the actuating ring is moved in translation along the axis with respect to the support.

The fourth helical surface is delimited by the drive slide.

The shaft has, at least in the longitudinal part thereof delimiting the second helical surface, a cross-section the contour of which is non-circular and, if appropriate, asymmetrical.

The second movement combines a rotation about the axis and a translation along the axis.

The support includes at least one cam, which rolls around the axis, preferentially with a helix angle greater than 84°, and which guides the mechanism in motion according to the second movement.

The first and second elements cooperate mechanically with each other so as to be locked in rotation about the axis relative to each other when the first and second helical surfaces mesh with each other.

One of the first and second elements includes at least one recessed pattern while the other of the first and second elements includes at least one protruding pattern that cooperates by shape matching with the recessed pattern(s) so as to lock in rotation the first and second elements.

The first and second elements form a second helical connection between therebetween, which, jointly with the first helical connection, locks the first and second elements in rotation relative to each other, and the mechanism is designed for acting simultaneously and in the same way on the first and second helical connections between the first and second elements.

BRIEF DESCRIPTION OF THE DRAWINGS

The invention will be better understood upon reading the following description, given only as an example and referring to the drawings, wherein.

DETAILED DESCRIPTION

FIGS. 1 to 5 show a surgical system 1 comprising an implant 10 and an instrument 20. As discussed in detail thereafter, the implant 10 and the instrument 20 incorporate fittings for connecting same directly to each other, in a reversible manner.

The implant 10 includes a body 11 that, for the purpose of the connection thereof to the instrument 20, delimits a bearing face 12 and a helical surface 13 extending recessed out from the bearing face 12. In the figures, the body 11 is shown very schematically, apart from the bearing face 12 thereof and the helical surface 13 thereof, without illustrating the multitude of conceivable embodiments related to the surgical purpose of the implant 10. In practice, the specificities of the implant 10, which are related to the functions thereof other than the function of the reversible connection thereof to the instrument 20, are not limiting, so that the body 11 of the implant can have, apart from the bearing face 12 and the helical surface 13 thereof, multiple and various fittings, not illustrated in the figures.

In all cases, the helical surface 13 is centered on a geometric axis X13 about which this helical surface winds, extending inside the body 11 from the bearing face 12. The helical surface 13 thus forms inside the body 11, a cavity 14, which is centered on the axis X13, and which opens axially onto the bearing face 12. The cavity 14 makes the implant 10 a female element.

According to an advantageous arrangement, the interest of which will appear thereafter, the body 11 of the implant 10 further includes one or a plurality of recessed patterns 15, herein in two copies, distinct from the cavity 14. In the example of embodiment considered in the figures, the recessed patterns 15 extend from the bearing face 12 of the body 11. Each recessed pattern 15 occupies a portion of the body 11 about the axis X13, the two recessed patterns 15 here being diametrically opposite one another with respect to the axis X13.

Figure 1:
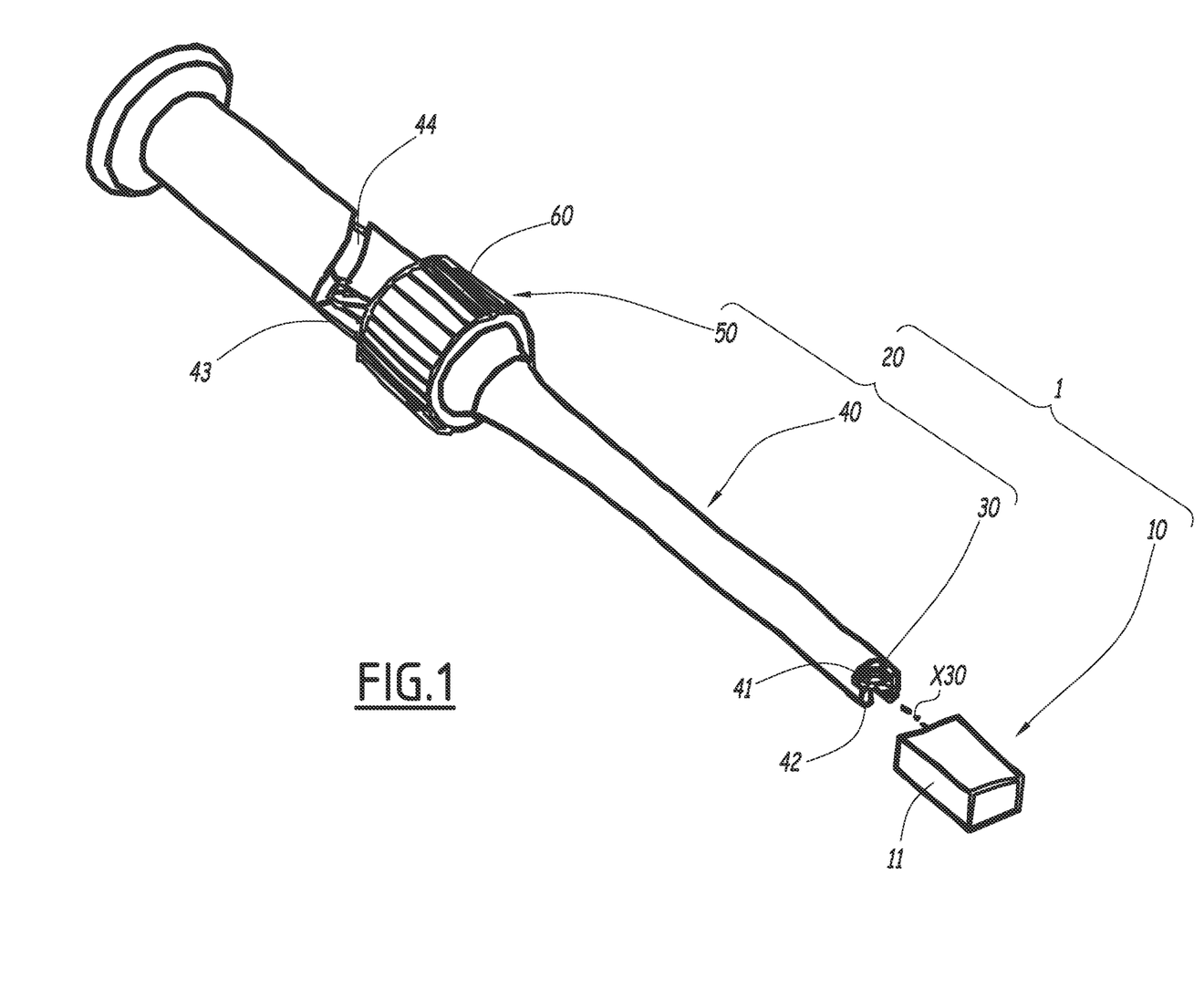
FIG. 1 is a perspective view of an embodiment of a surgical system according to the invention.
Figure 2:
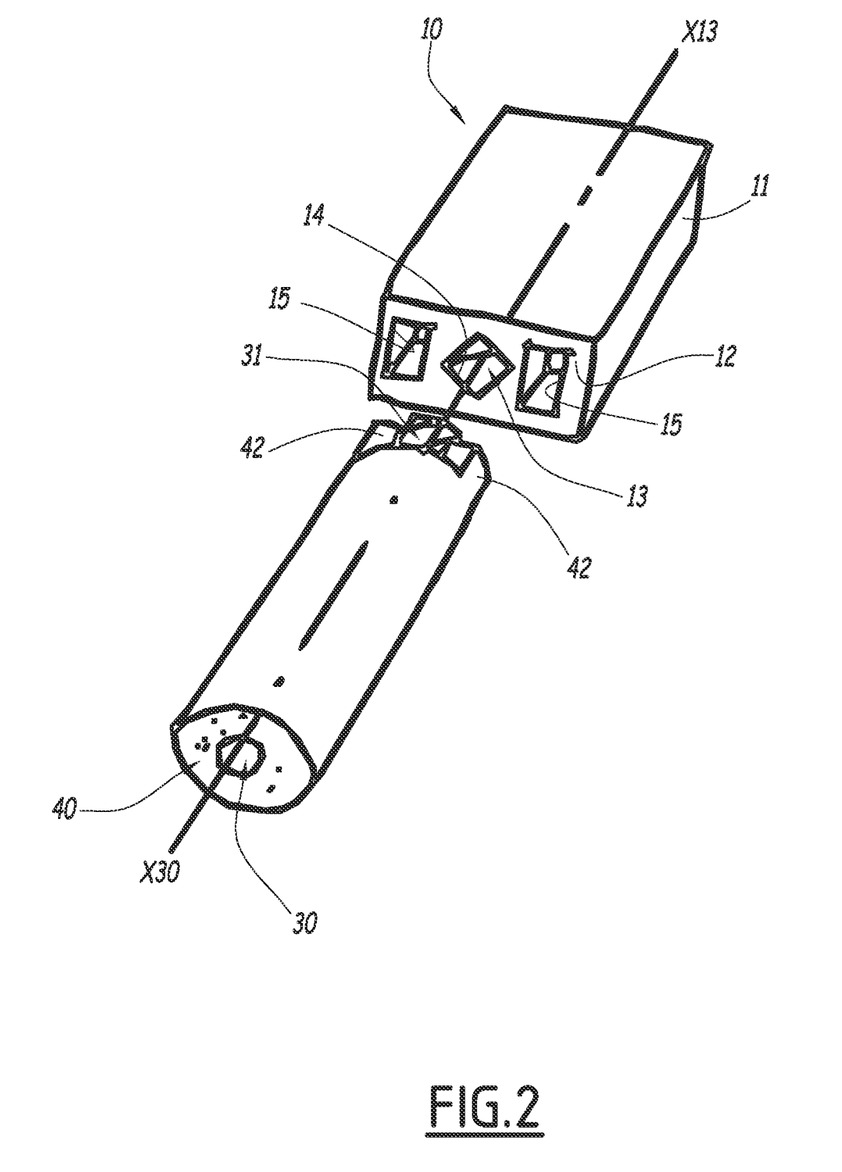
FIG. 2 is a view similar to FIG. 1, partially illustrating the surgical system at a different angle of view from the angle of FIG. 1.
Figure 3:
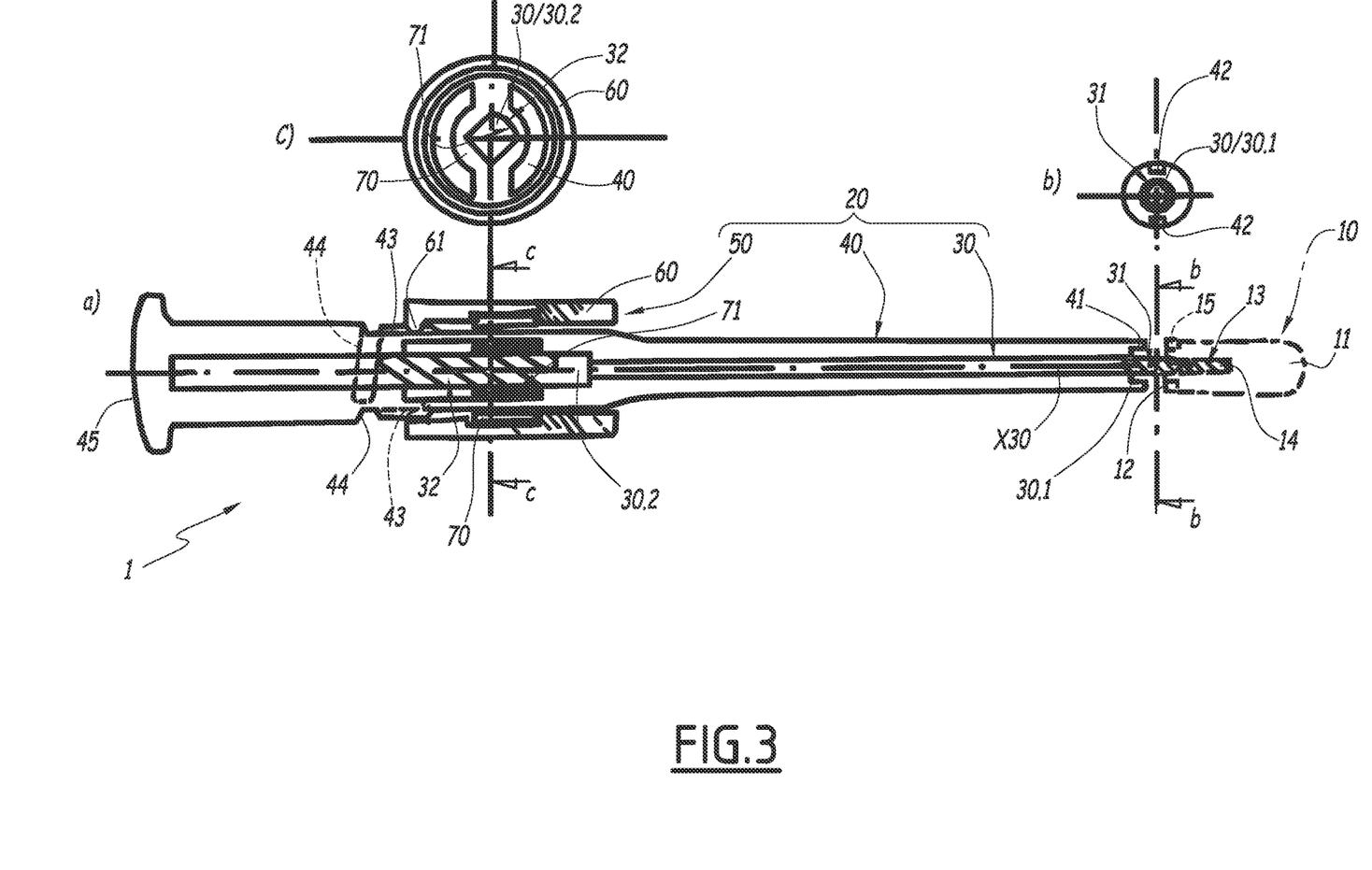
FIG. 3 shows together an insert a), which is a longitudinal section of the system shown in FIG. 1, an insert b), which is a section along the line b-b shown on the insert a), and an insert c), which is a section along the line c-c shown on the insert a)
Figure 4:
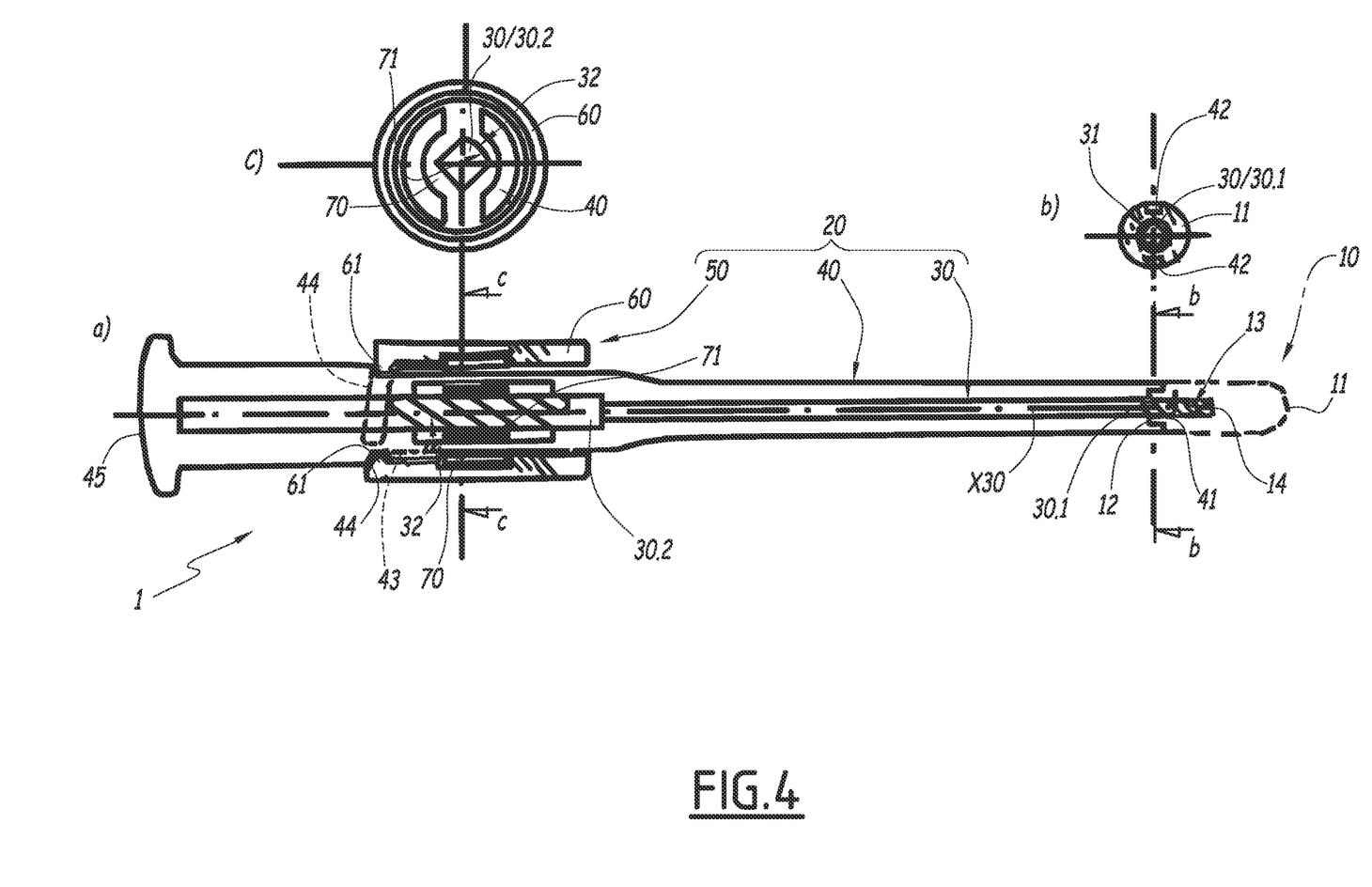
FIGS. 4 and 5 are views similar to FIG. 3, FIGS. 3 to 5 correspondingly illustrating three configurations successively implemented when using the surgical system.
Figure 5:
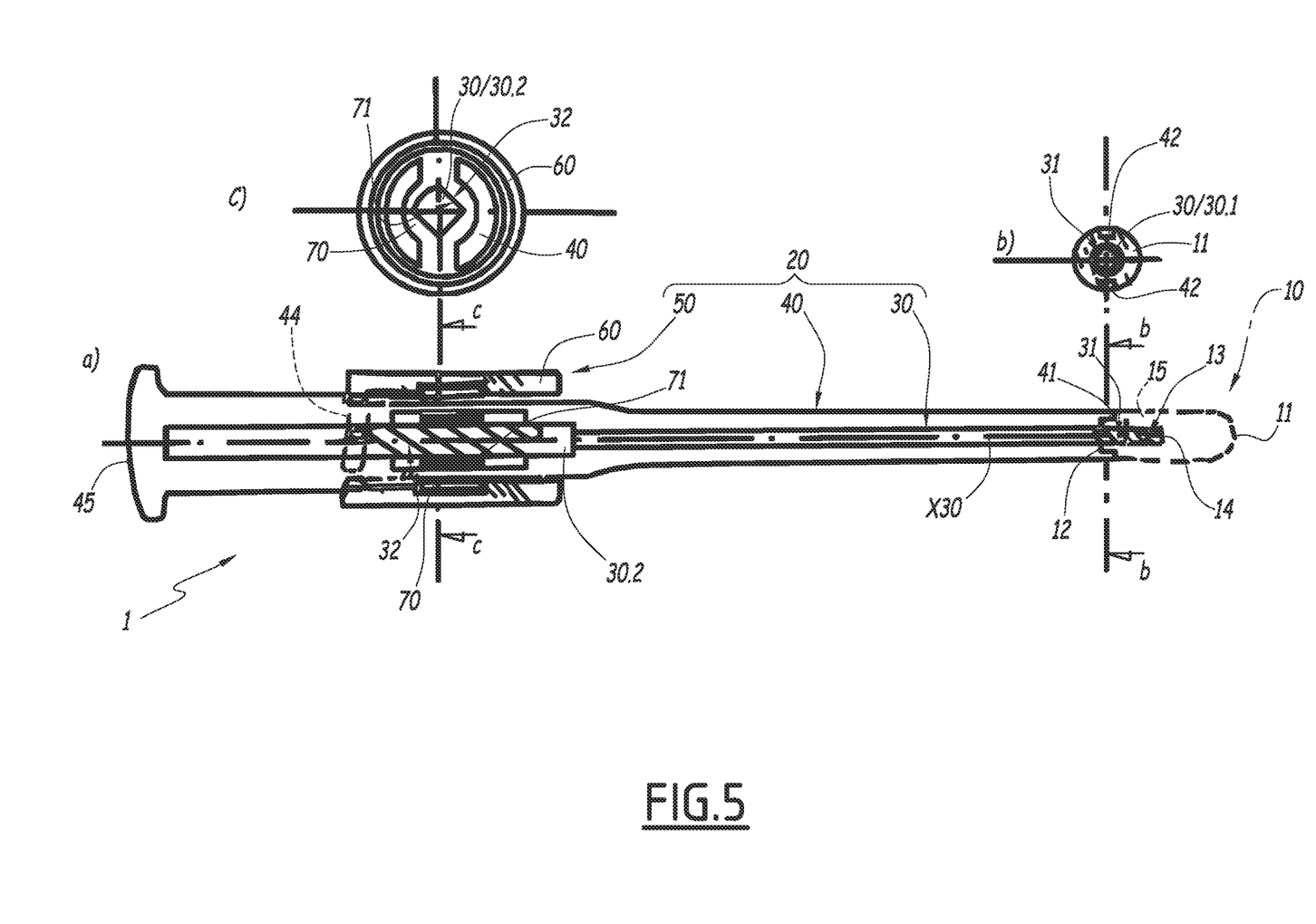

The instrument 20 includes a shaft 30, which can be well seen in FIGS. 3 to 5 and which is only marginally visible in FIGS. 1 and 2.

The shaft 30 defines a geometric axis X30, on which the shaft is centered and along which the shaft extends in length. As can be seen clearly in FIGS. 3 to 5, the shaft 30 delimits externally, i.e. on the external lateral face thereof, two helical surfaces 31 and 32 distinct from each other, which are centered on the axis X30 and which are wound about the shaft 30, by forming respective portions of the outer lateral face therein. The helical surfaces 31 and 32 occupy respective longitudinal parts 30.1 and 30.2, which are distinct from each other, being distributed on the shaft 20 along the axis X30. The longitudinal part 30.1, which delimits the helical surface 31, forms a longitudinal end part of the shaft 20, while the longitudinal part 30.2, which delimits the helical surface 32, forms either a longitudinal end part of the shaft, axially opposite the longitudinal part 30.1, or an intermediate longitudinal part of the shaft.

The helical surface 31 is congruent with the helical surface 13 of the implant 10 so that, when the helical surfaces 31 and 13 are made coaxial with each other and are rotated about the axes X30 and X13 thereof, the helical surfaces 31 and 13 mesh, or mate, with each other, inducing the relative axial displacement thereof, in a reversible way. In other words, the helical surfaces 31 and 13 form a helical connection between the implant 10 and the instrument 20, more precisely between the body 11 of the implant and the shaft 30 of the instrument.

The instrument 20 further include a support 40 on which the shaft 21 is mounted so as to be apt to move, as discussed in detail hereinafter.

In the example of embodiment considered in the figures, the support 40 has a generally tubular shape, inside which the shaft 30 is mounted coaxially. Whatever the shape of the support 40, the shaft 30 is mounted on the latter both in a fixed manner along the axis X30 and so as to rotate freely about the axis X30. In other words, the shaft 30 and the support 40 are fixedly connected in translation to one another along the axis X30, while being free to rotate about said axis with respect to each other. In practice, various embodiments are conceivable for providing the connection between the shaft 30 and the support 40. In the non-limiting example considered in the figures, the shaft 30 has shouldered surfaces that are arranged in axial abutment against matching shouldered surfaces, provided inside the tubular wall of the support 40, without the inner face of the tubular wall interfering with the shaft 30 along a direction peripheral to the axis X30. In practice, the relative rotational movements between the shaft 30 and the support 40 are advantageously guided, e.g. by one or a plurality of bearings or similar fittings, so as to set the position of the axis X30 with respect to the support 40 when the shaft 30 is mounted on the support.

Moreover, whatever the embodiment of the support 40, the latter delimits a bearing face 41. In the mounted state of the shaft 30 on the support 40, the bearing face 41 is arranged transversely to the axis X30 and the longitudinal end part 30.1 of the shaft 30 emerges axially from the bearing face 41, as is clearly visible in FIGS. 1 to 3. Thus, the helical surface 31 extends from the bearing face 41, being arranged so as to protrude from the latter, which makes instrument 20 a male element.

The bearing face 41 matches the bearing face 12 of the implant 10. As a result, when the helical surfaces 31 and 13 mesh with each other in such a way that the axial displacement thereof, induced by the mating thereof, brings the implant 10 and the instrument 20 axially closer to each other, the bearing faces 41 and 12 move axially toward each other until same cooperate with each other by matching shapes: the aforementioned axial approach coming closer between the bearing faces 41 and 12 results in the bearing faces 41 and 12 being juxtaposed against each other as in FIG. 4, then being pressed axially against each other as in FIG. 5, thus being pressed firmly against each other, which leads in particular to a rigid attachment effect between the support 40 and the implant 10, by rubbing contact between the bearing faces 41 and 12, and which tends to eliminate any residual play between the bearing faces.

According to an advantageous arrangement, the support 40 further includes one or a plurality of protruding patterns 42, herein two. The protruding patterns 42 match the recess patterns 15 of the implant 10 so that, when the helical surfaces 31 and 13 mate with each other so as to bring the bearing faces 41 and 12 closer to each other, the protruding patterns 42 cooperate by matching shapes with the recessed patterns 15 so as to lock in rotation the support 40 and the implant 10 with respect to each other, about the axis X30. Such cooperation by matching shapes, between the protruding patterns 42 and the recessed patterns 15 consists herein, in that the protruding patterns 42 are axially received inside the recessed patterns 15 in an adjusted way therebetween, as shown diagrammatically in FIGS. 4 and 5. It is understood that the geometrical specificities of the protruding patterns 42 and of the recessed patterns 15 are not limiting as long as the protruding patterns 42 and the recessed patterns 15 are shaped so as to cooperate by matching shapes for the purpose of locking in rotation the support 40 and of the implant 10 with respect to each other, about the axis X30. According to a practical embodiment, which is implemented in the example illustrated in the figures, the protruding patterns 42 extend from the bearing face 41.

The instrument 20 further includes a mechanism 50 for controlling the reversible connection between the implant 10 and the instrument 20. The mechanism 50 is designed for acting on the helical connection formed by the helical surfaces 13 and 31 between the implant 10 and the instrument 20, as explained hereinafter.

In the embodiment considered in the figures, the mechanism 50 includes an actuating ring 60 and a drive slide 70.

The actuating ring 60 is mounted on the support 40 while being guided in motion with respect to the support 40 according to two distinct movements that are implemented successively when the mechanism 50 is actuated, namely:

- a first movement, by which the actuating ring 60 moves, with respect to the support 40, from position thereof shown in FIG. 3 to the position thereof shown in FIG. 4, and which includes a translation movement along the axis X30 without involving any rotation about said axis, and
- a second movement, by which the actuating ring 60 moves, with respect to the support 40, from the position thereof shown in FIG. 4 to the position thereof shown in FIG. 5, and which combines a rotation about the axis X30 and a translation along said axis.

In the example considered in the figures, the actuating ring 60 surrounds the tubular wall of the support 40, at an intermediate part of the latter along the axis X30. For the purpose of guiding the actuating ring 60 in motion with respect to the support 40 according to the first and second movements, the inner face of the actuating ring 60 cooperates by contact with the outer face of the tubular wall of the support 40: to this end, the inner face of the actuating ring 60 is e.g. provided with one or a plurality of protruding pins 61, herein in two diametrically opposite units along the inner periphery of the actuating ring 60, the protruding pins 61 being correspondingly engaged in guide tracks, delimited by the outer face of the tubular wall of the support 40 and each including both a rectilinear slide 43 which extends parallel to the axis X30 and which guides the actuating ring 60 according to the first movement, and a cam 44 which rolls around the axis X30 and guides the actuating ring 60 according to the second movement. For reasons which will appear thereafter, the cams 44 preferentially have a helix angle greater than about 84° so that the translational component of the second movement has a much smaller value than the value of the rotational component of the second movement; i.e. when the actuating ring 60 travels the total stroke thereof following the second movement, the ring mainly performs a rotational movement about the axis X30 and marginally a translational movement along said axis. Moreover, according to a preferred design, each cam 44 rolls around the axis X30 over less than 360°, or preferentially less than 180°, so that when the actuating ring 60 travels the total stroke thereof following the second movement, the ring makes less than one revolution on itself, even preferentially less than a half-turn on itself: in this way, when the mechanism 50 is actuated, the user can rotate the actuating ring 60 with a single hand and with one movement, so that said actuating ring 60 then travels the entire stroke thereof following the first movement and then the second movement.

The embodiment that has just been described for the guide tracks associating the rectilinear slides 43 and the cams 44 is not limiting. Multiple embodiments are conceivable for guiding the actuating ring 60 in motion with respect to the support 40 according to successively the first and second movements, or more generally, for actuating the mechanism 50 successively according to the first and second movements, in particular with the second movement which is mainly rotational and the total angular travel of which is less than 360°, preferentially less than 180°.

The drive slide 70 is mounted on the support 40 both fixed in rotation about the axis X30 and apt to translate freely along said axis. The drive slide 70 is thus linked in rotation to the support 40, about the axis X30, while being free in translation along the axis X30 with respect to the support 40. To this end, in the embodiment considered in the figures, the drive slide 70 is axially slipped into the support 40, being arranged radially on both sides of the tubular wall of the support 40, where it should be noted that, as clearly visible on the inserts c) shown in FIGS. 3 to 5, the drive slide 70 includes transverse portions which are received in through passages of the annular wall of the support 40, which blocks the drive slide 70 in rotation about the axis X30 with respect to the support 40. Of course, multiple other embodiments are conceivable in this respect.

Moreover, the drive slide 70 is mounted on the actuating ring 60 so as to be linked in translation along the axis X30 to the actuating ring 60 while being free to rotate about the axis X30 with respect to the actuating ring. For this purpose, in the example considered in the figures, the drive slide 70 is mounted inside the actuating ring 60, being received in a notch delimited by the inner periphery of the actuating ring so as to be apt to rotate freely therein with respect to the actuating ring while being in axial abutment against the axial ends of the aforementioned notch. Here again, of course, multiple embodiments, which are alternatives to the embodiment which has just been described, are conceivable in this respect.

Furthermore, the drive slide 70 cooperates by contact with the shaft 30 so as to rotate the shaft 30 about the axis X30 with respect to the support 40 when the drive slide 70 is moved in translation along the axis X30 with respect to the support 40, in other words, when the actuating ring 60 is translated along the axis. To this end, in the example considered in the figures, the drive slide 70 delimits, herein internally, a helical surface 71 which is congruent with the helical surface 32 of the shaft 30 so that, when the helical surfaces 71 and 32 are made coaxial with each other and rotated about the axis X30, the helical surfaces 71 and 32 mesh with each other, inducing the relative axial displacement thereof, in a reversible way. In other words, the helical surfaces 32 and 71 form a helical connection between the shaft 30 and the drive slide 70, in other words, more generally, a helical connection between the shaft 30 and the mechanism 50.

Here again, although embodiments such as the embodiment described hereinabove are preferred, in which a helical connection is provided between the shaft 30 and the mechanism 50, other embodiments are conceivable for rotating the shaft 30 about the axis X30 with respect to the support 40, when the mechanism 50 is actuated in translation along the axis X30.

Other features and advantages of the surgical system 1 will appear hereinafter in the description of an example of using the surgical system to directly connect the implant 10 and the instrument 20 to each other. Such use is typically performed by a surgeon during the intraoperative time.

The implant 10 and the instrument 20 are initially considered to be separated from each other. A surgeon then handles the instrument 20 so as to align the axes X30 and X13 and to axially introduce the free end of the longitudinal end portion 30.1 of the shaft 30 inside the cavity 14 of the implant 10. The surgical system 1 is then in the configuration illustrated in FIG. 3. In the configuration shown in FIG. 3, the actuating ring 60 occupies a position corresponding to the starting point of the total stroke thereof following the first and second successive movements described hereinabove. In other words, herein, the pins 61 of the actuating ring 60 are correspondingly located at the axial end of the rectilinear slides 43, opposite the cams 44.

The surgeon then actuates the mechanism 50 according to the first aforementioned movement, moving the surgical system 1 from the configuration shown in FIG. 3 to the configuration shown in FIG. 4. More precisely, the surgeon moves the actuating ring 60 according to the first movement, i.e. exclusively in translation along the axis X30, which translates drive slide 70 in a corresponding manner and hence rotates the shaft 30 about the axis X30. Such setting in rotation of the shaft 30 leads to the mating of the helical surface 31 thereof with the helical surface 13 of the implant 10 and, as a result, the axial displacement of the implant 10 toward the instrument 20, by bringing the bearing faces 12 and 41 axially toward each other. Herein, the relative axial displacement between the implant 10 and the instrument 20 further leads to the cooperation of the recessed patterns 15 and of the protruding patterns 42, which, without any additional intervention from the surgeon, locks in rotation the implant 10 and the instrument 20 with respect each other, about the axis X30, in order to prevent an ineffective mating of the helical surfaces 31 and 13.

When the actuating ring 60 has traveled the entire rectilinear stroke thereof according to the first movement, i.e. when the pins 61 of the actuating ring reach the end of the rectilinear slides 43, turned toward the cams 44, the surgical system 1 is in the configuration shown FIG. 4. In such configuration, the bearing faces 12 and 41 are juxtaposed axially against one another, forming a contact interface that is arranged transversely to the axis X30. Thus, when the mechanism 50 is actuated according to the first movement, the mechanism 50 mates the helical surfaces 13 and 31 with each other until the bearing faces 12 and 41 are juxtaposed axially against each other.

The surgeon then actuates the mechanism 50 according to the second aforementioned movement, moving the surgical system from the configuration shown in FIG. 4 to the configuration shown in FIG. 5. More precisely, the surgeon moves the actuating ring 60 according to the second movement, i.e. in a combined manner, mainly in rotation about the axis X30 and marginally in translation along the axis X30. The rotational component of the second movement angularly shifts the actuating ring 60 with respect to the support 40, thereby preventing the axial displacement of the actuating ring in a direction opposite to the direction of the first movement and thereby preventing the helical surfaces 13 and 31 from disengaging. At the same time, the translational component of the second movement induces, according to the same considerations as those developed hereinabove for the first movement, an additional mating of the helical surfaces 13 and 31 and, consequently, an axial pressing of the bearing faces 12 and 41 against each other; in other words, the shaft 30 is tensioned along the axis X30, by axially pulling the implant 10 in tight abutment against the support 40 of the instrument 20 at the contact interface between the bearing faces 12 and 41.

When the actuating ring 60 has traveled the stroke according to the second movement, i.e. when the pins 61 of the actuating ring 60 reach the end of the cams 44 opposite the rectilinear slides 43, the surgical system is in the configuration shown in FIG. 5. In the configuration shown in FIG. 5, the helical surfaces 13 and 31 are prevented from disengaging, thus locking the corresponding helical connection, and the bearing faces 12 and 41 are pressed firmly against each other in the direction of the axis X30. Thus, when the mechanism 50 is actuated according to the second movement, following the first movement, the mechanism 50 locks the helical connection between the implant 10 and the instrument 20, while axially pressing the bearing faces 12 and 41 against each other.

As long as the surgical system 1 is in the configuration shown in FIG. 5, the implant 10 is firmly rigidly attached to the instrument 20, being totally immobilized with respect to the latter and being used for the transmission of stresses therebetween via the interface formed by the bearing faces 12 and 41. As a non-limiting example, the surgeon can then move the instrument 20 in space, so as to implant the implant 10 in the body of a patient, in particular by accurately positioning the implant 10 in the body of the patient and, where appropriate, by force-fitting or wedging the implant at an anatomical structure of the patient. In this respect, in the embodiment considered in the figures, the support 40 includes, in the region thereof axially opposite the bearing face 41, an impaction face 45 against which the surgeon can apply impaction forces for the purpose of implanting the implant 10 in the patient's body.

When the surgeon so wishes, in particular once the implant 10 is implanted in the patient's body, the instrument 20 is disconnected from the implant 10, in particular without modifying the position of the latter with respect to the patient's body. To this end, the surgeon actuates the mechanism 50 in a reverse manner compared to the actuation performed for connecting the implant 10 and the instrument 20 to each other. Thus, the mechanism 50 is first actuated along an inverse movement to the second aforementioned movement, which moves the surgical system from the configuration shown in FIG. 5 to the configuration shown in FIG. 4, then the mechanism 50 is actuated in an additional movement, inverse to the first aforementioned movement, which moves the surgical system 1 from the configuration shown in FIG. 4 to the configuration shown in FIG. 3. The instrument 20 is thus released from the implant 10.

Taking into account the explanations given so far, it is understood that the surgical system 1 is particularly easy to handle for the surgeon. Moreover, when the surgical system 1 is in the configuration shown in FIG. 5, the connection between the implant 10 and the instrument 20 is secured. Moreover, when the implant 10 and the instrument 20 are disconnected, they can be easily cleaned and/or decontaminated; for this purpose, the shaft 30, the support 40 and the mechanism 50 can be designed for being easily disassembled.

Such performance of the surgical system 1 is obtained without the system needing to use any threaded connection. On the other hand, the connection between the implant 10 and the instrument 20 is achieved by the helical connection formed by the helical surfaces 13 and 31, which are not a thread and a tapping of a standardized threaded connection. The same applies to the helical connection between the shaft 30 and the mechanism 50, formed by the helical connections 32 and 71. In particular, according to a preferred design which makes the surgical system 1 work as described hereinabove, the helix angle of the helical connection between the implant 10 and the instrument 20 and/or of the helical connection between the shaft 30 and the mechanism 50 is comprised between 6° and 45°, preferentially between 10° and 40°, preferentially between 15° and 45°. In practice, the helix angle of the helical connection between the implant 10 and the instrument 20 can be identical to or different from the helix angle of the helical connection between the shaft 30 and the mechanism 50. When the two helix angles are different, the helix angle of the helical connection between the implant 10 and the instrument 20 is preferentially greater than the helix angle of the helical connection between the implant 10 and the instrument 20. In all cases, the non-threaded helical shape of the aforementioned helical connections makes it possible to produce, by additive manufacturing, typically by 3D printing, the helical surfaces 13, 30, 31 and 71 and, more generally, a part or even all of the implant 10 and/or of the instrument 20.

Figure 6:
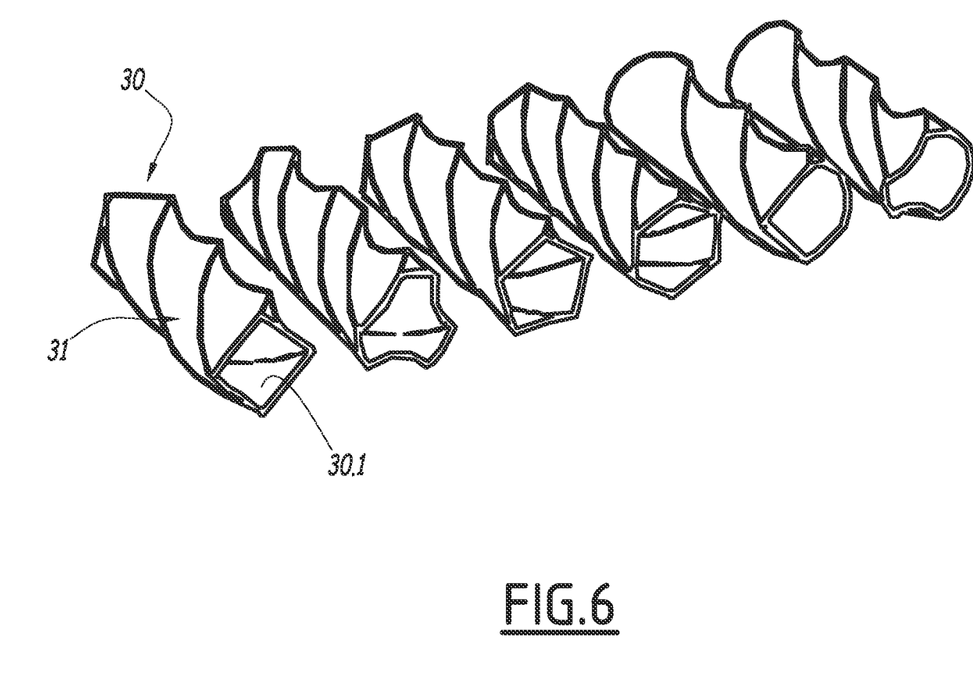
FIG. 6 is a perspective view illustrating various embodiments for a part of the surgical system.
Figure 7:
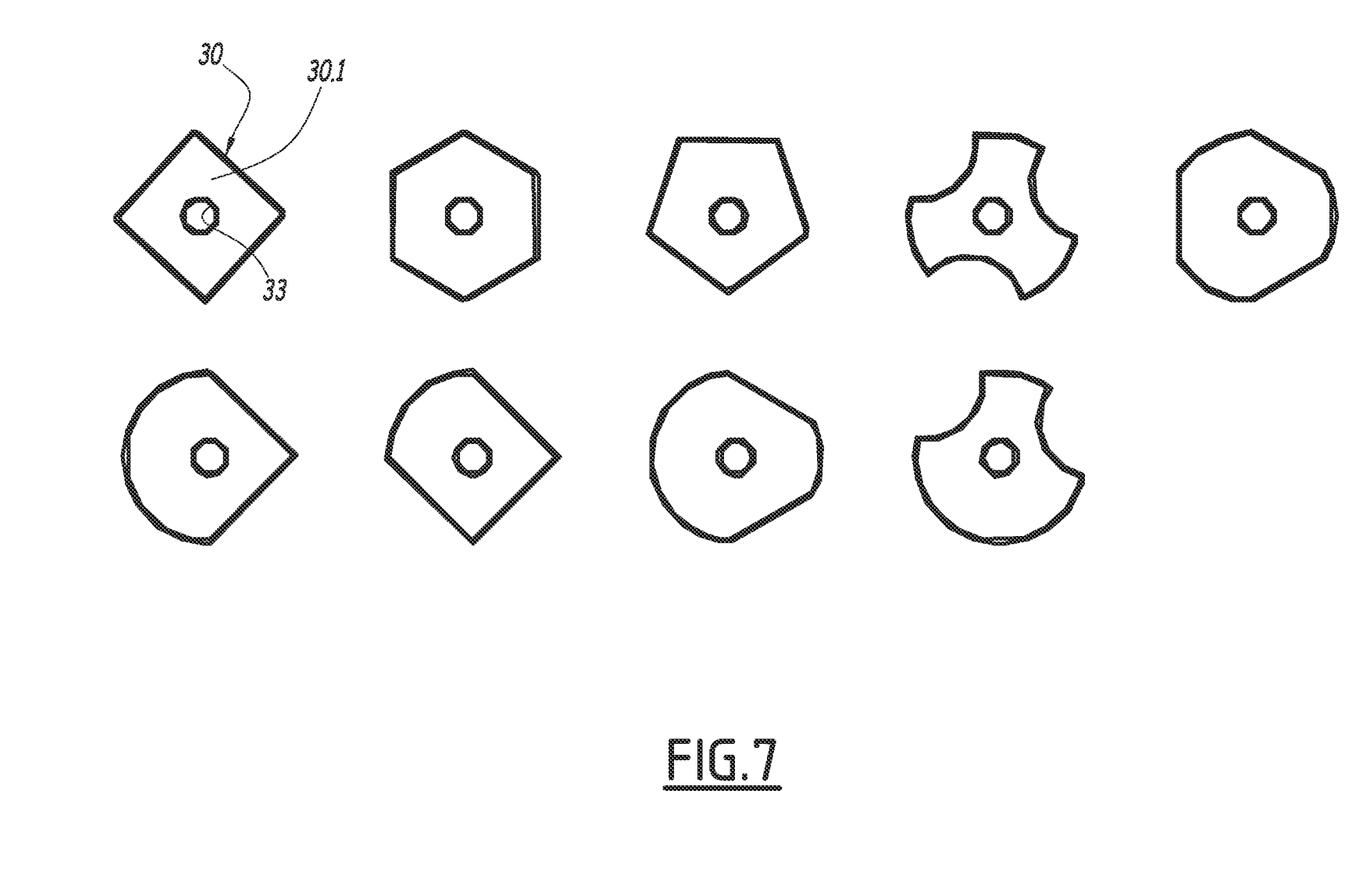
FIG. 7 is an plan view also illustrating various embodiments for a part of the surgical system.

In the extension of the foregoing considerations, FIGS. 6 and 7 illustrate the multitude of embodiments possible for the part of the shaft 30 delimiting the helical surface 31, i.e. herein, the longitudinal end part 30.1 of the shaft. Of course, the multitude of embodiments is found, by congruence, for the part of the cavity 14 delimiting the helical surface 13. Thus, as illustrated by FIGS. 6 and 7, the cross-section of the part of the shaft 30, delimiting the helical surface 31, advantageously has a non-circular contour, as shown in the first four examples of FIG. 6, wherein the contour is square, multilobed, pentagonal and hexagonal, respectively. Such cross-section can even have an asymmetrical contour, as illustrated in the last two examples of FIG. 6: such asymmetry then acts as a foolproof means for the engagement of the helical surface 31 with the helical surface 13. Moreover, as an optional fitting illustrated in FIG. 7, the shaft 30 can be fluted, i.e. provided with a spline 33 crossing axially right along it.

Although not illustrated, considerations similar to those developed in the preceding paragraph apply for the part of the shaft 30 delimiting the helical surface 32 and, congruently, for the part of the drive slide 70 delimiting the helical surface 71.

Figure 8:
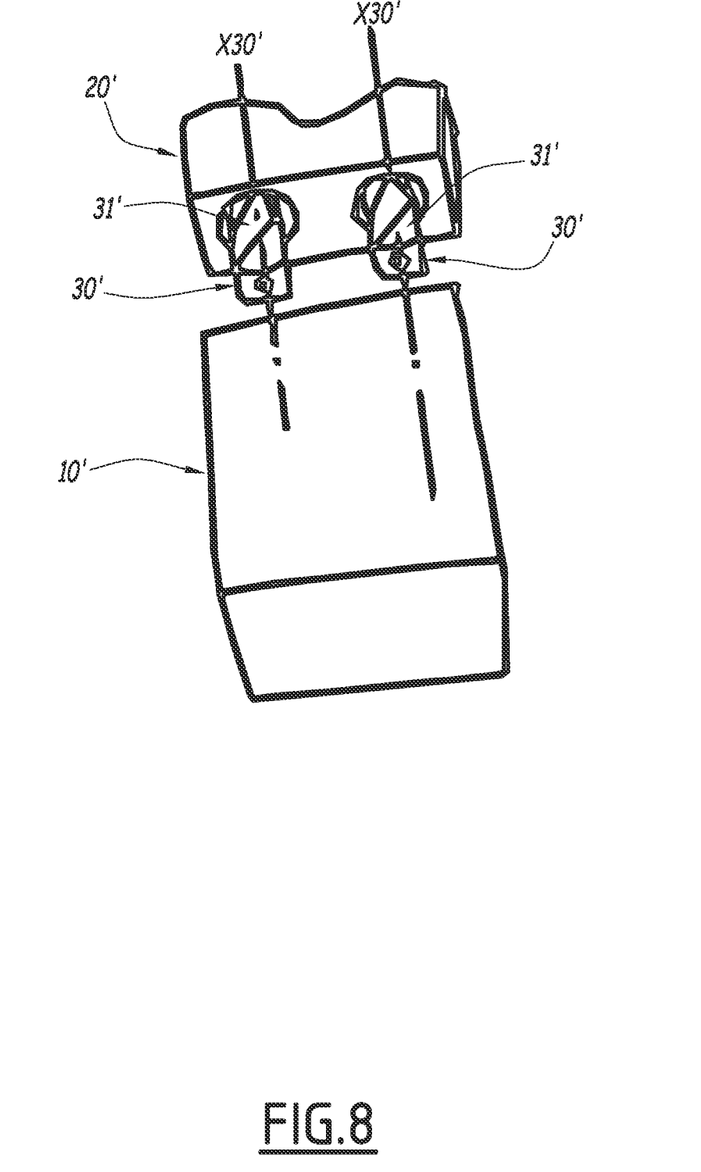
FIGS. 8 and 9 are perspective views, from different angles of observation, of a second embodiment of the surgical system according to the invention.
Figure 9:
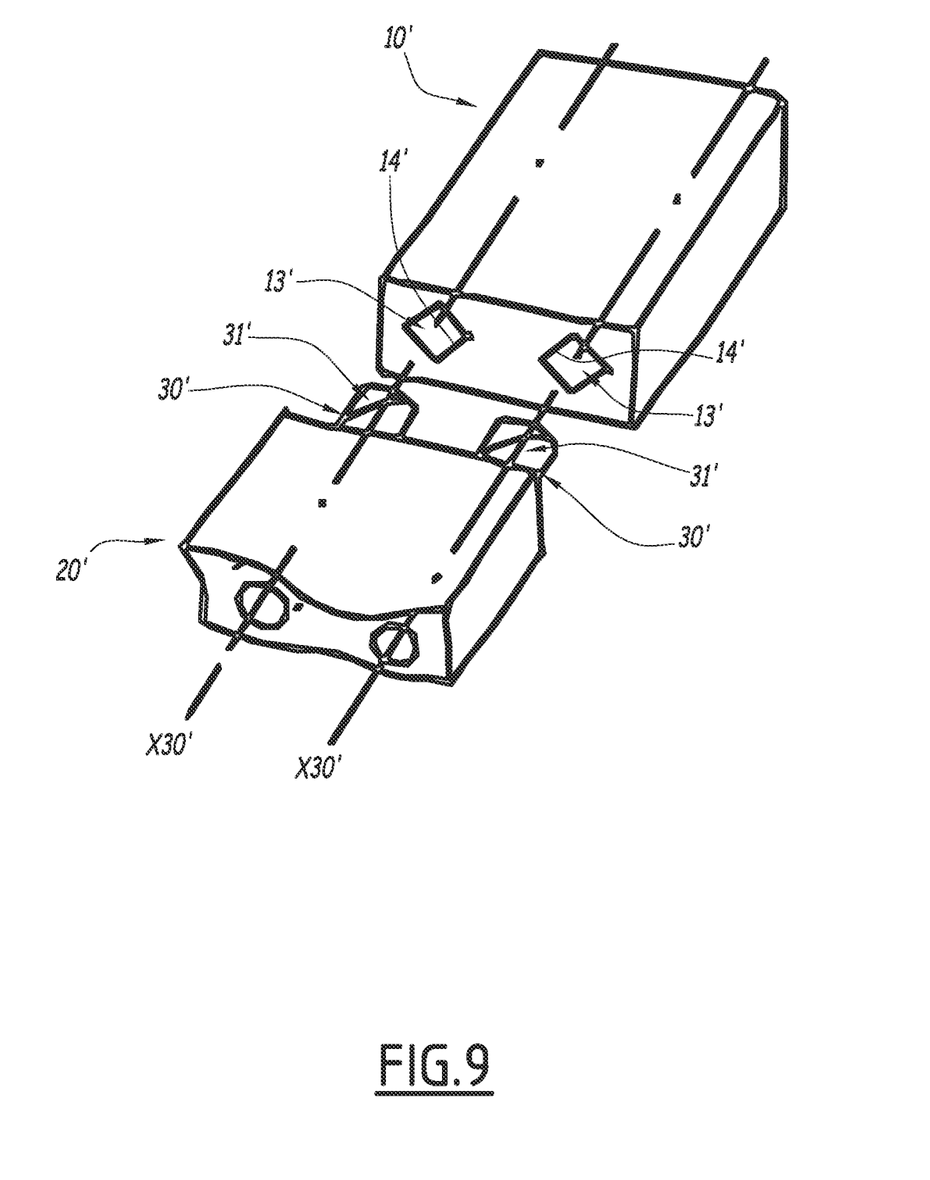

FIGS. 8 and 9 show an alternative embodiment to the surgical system 1, which is referenced by 1'. The surgical system 1' comprises an implant 10' and an instrument 20', which are functionally or structurally similar to the implant 10 and the instrument 20, while being differentiated from the latter by the way in which the implant and the instrument are locked in rotation with respect to each other, about the axis X30. More precisely, the implant 10' and the instrument 20' do not have any recessed and protruding patterns such as the recessed patterns 15 and protruding patterns 42 of the implant 10 and of the instrument 20. At the same time, the instrument 20' does not include only one shaft, like the shaft 30, but has two shafts 30', which are each functionally or structurally similar to the shaft 30 and the respective axes X30' which are parallel to each other. In particular, each shaft 30' delimits a helical surface 31' which is functionally, or even structurally similar to the helical surface 31 of the shaft 30. Correspondingly, the implant 10' includes two cavities 14', each of which is functionally or even structurally similar to the cavity 14 and in each of which the implant 10' delimits a helical surface 13', which is functionally or even structurally similar to the helical surface 13. Thus, the helical surfaces 31' are correspondingly congruent with the helical surfaces 13' and form with the latter, two helical connections between the implant 10' and the instrument 20', each of the two helical connections being functionally, or even structurally similar to the helical connection between the implant 10 and the instrument 20. Due to the presence of the two helical connections, the latter lock the implant 10' and the instrument 20' in rotation with respect to each other, about each of the axes X30', when the helical surfaces 31' mesh, or mate, with the helical surfaces 13'.

In practice, the instrument 20' includes a mechanism, not shown in the figures, which is functionally similar to the mechanism 50 of the instrument 20, with the advantageous specificity that said mechanism of the instrument 20' is designed for acting simultaneously and in the same way on the two helical connections between the implant 10' and the instrument 20'.

Finally, various fittings and variants of the surgical systems 1 and 1' described up to now are further conceivable. Examples include:
the male/female relation between the implant 10 or 10' and the instrument 20 or 20' can be reversed; the same is true for the recessed patterns 15 and the protruding patterns 42; and/or
other types of manufacturing than additive manufacturing can be used to manufacture all or part of the implant 10 or 10' and/or the instrument 20 or 20'; and/or
rather than the second aforementioned movement combining rotational and translational components, like in the example described hereinabove, the second movement can be provided as exclusively rotational, i.e. rotational about the axis X30, X30' without being a translation along said axis; in such case, the mechanism 50 is suitable so that the actuation thereof according to the second exclusively rotational movement locks the helical connection between the implant 10 and the instrument 20, preventing the disengagement of the helical surfaces 13 and 31, while ensuring that, at the end of the second exclusively rotational movement, the bearing faces 12 and 41 are pressed axially against each other, such abutment of the bearing faces 12 and 41 being either reached at the end of the first movement and maintained during the second movement, or obtained progressively during the second movement, in both cases through ad hoc fittings of the mechanism; and/or
rather than the two components of the surgical system 1 or 1', which can be directly connected to each other, being a surgical implant and a surgical instrument, such as the implant 10 or 10' and the instrument 20 or 20', the two elements of the surgical system can be two surgical implants which are e.g. to be connected directly to each other during a surgical intervention.

The invention claimed is:

1. A surgical system, comprising first and second elements which are either two surgical implants or a surgical implant and a surgical instrument,
wherein the first element includes:
a first bearing face, and
a first helical surface which extends from the first bearing face,
and wherein the second element includes:
a second bearing face, which matches the first bearing face,
a second helical surface, which extends from the second bearing face and which is congruent with the first helical surface so that the first and second helical surfaces form a first helical connection between the first and second elements, centered on an axis, and
a mechanism for controlling reversible connection between the first and second elements, the mechanism being suitable for being actuated successively:
along a first movement, which includes a translation along the axis without involving rotation about the axis and by which the mechanism causes the first and second helical surfaces to mesh with each other until the first and second bearing faces are axially juxtaposed against each other, and
along a second movement, which includes a rotation about the axis and by which the mechanism locks the first helical connection while the first and second bearing faces are pressed axially against each other.

2. The surgical system of claim 1, wherein the first helical connection between the first and second elements has a helix angle comprised between 6° and 45°.

3. The surgical system according to claim 1, wherein the first helical surface extends recessed inside the first bearing face, and wherein the second helical surface is arranged protruding from the second bearing face.

4. The surgical system according to claim 3, wherein the second element includes:
a shaft which is centered on the axis and which externally delimits the second helical surface, and
a support which delimits the second bearing face, on which the shaft is mounted both in a fixed manner along the axis and so as to freely rotate about the axis, and on which the mechanism is mounted movable so as to be actuatable according to the first and second movements and to rotate the shaft about the axis with respect to the support when the mechanism is actuated in translation along the axis.

5. The surgical system according to claim 4, wherein the shaft externally delimits a third helical surface, which is distinct from the second helical surface,
and wherein the mechanism delimits a fourth helical surface which is congruent with the third helical surface so that the third and fourth helical surfaces form a helical connection between the shaft and the mechanism.

6. The surgical system according to claim 4, wherein the mechanism includes an actuating ring, which is guided in motion with respect to the support according to the first and second movements, and wherein the mechanism further includes a drive slide which is:
- linked in rotation to the support, about the axis, while being free in translation along the axis with respect to the support,
- linked in translation to the actuating ring, along the axis, while being free to rotate about the axis with respect to the actuating ring, and
- suitable for rotating the shaft about the axis with respect to the support when the actuating ring is moved in translation along the axis with respect to the support.

7. The surgical system according to claim 4, wherein the shaft has, at least in the longitudinal part thereof delimiting the second helical surface, a cross-section, the contour of which is non-circular.

8. The surgical system according to claim 4, wherein the shaft has, at least in the longitudinal part thereof delimiting the second helical surface, a cross-section, the contour of which is asymmetrical.

9. The surgical system according to claim 4, wherein the second movement combines a rotation about the axis and a translation along the axis, wherein the support includes at least one cam, which rolls around the axis, and which guides the mechanism in motion according to the second movement.

10. The surgical system according to claim 9, wherein the at least one cam has a helix angle greater than 84°.

11. The surgical system according to claim 1, wherein the second movement combines a rotation about the axis and a translation along the axis.

12. The surgical system according to claim 1, wherein the first and second elements mechanically cooperate with each other so as to be locked in rotation with respect to each other about the axis when the first and second helical surfaces mesh with each other.

13. The surgical system according to claim 12, wherein one of the first and second elements includes at least one recessed pattern while the other of the first and second elements includes at least one protruding pattern which cooperates by shape matching with the recessed pattern(s) so as to lock in rotation the first and second elements.

14. The surgical system of claim 12, wherein the first and second elements form a second helical connection therebetween which jointly with the first helical connection, locks in rotation the first and second elements with respect to each other and wherein the mechanism is suitable for acting simultaneously and in the same way on the first and second helical connections between the first and second elements.

* * * * *